US00PP08824P

United States Patent [19]

Probasco

[11] Patent Number: Plant 8,824

[45] Date of Patent: Jul. 5, 1994

[54] HOP PLANT NAMED 37 H87203-1"

[75] Inventor: Gene Probasco, Yakima, Wash.

[73] Assignee: John I. Haas, Inc., Yakima, Wash.

[21] Appl. No.: 993,068

[22] Filed: Dec. 17, 1992

[51] Int. Cl.[5] ..... A01H 5/00
[52] U.S. Cl. ..... Plt./100
[58] Field of Search ..... Plt. 100

[56] References Cited

PUBLICATIONS

John I. Haas Co., Inc. "Farming" 1987 30 pages.
John I. Haas Co., Inc. "U.S. Hop Industry Information Manual" 1985 13 Pages.
John I. Haas Co., Inc. "Hop Research & Development" 1989 9 Pages.
John I. Haas Co., Inc. "Hop Pellets—Regular and Concentrated/Technical Data" 1985 9 Pages.
John I. Haas Co., Inc. "Non-Isomerized Hop Extract—Technical Data" 1985 13 Pages.
John I. Haas Co., Inc. "Isomerized Hop Extract—Technical Data" 1985 9 Pages.
John I. Haas Co., Inc. "Hop Varieties—U.S. Grown" 8 Pages.

*Primary Examiner*—James R. Feyrer
*Attorney, Agent, or Firm*—Stratton Ballew Richardson

[57] ABSTRACT

A new variety of hop plant (H87203-1) originating as the result of a controlled corss pollination between unpatented Galena female hop plant with unpatented John I. Haas, Inc. (Haas) male hop plant No. 833-53M, and unique particularly for its cones' unusually high percentage of beta acids when compared to its female parent variety Galena (unpatented) and otherwise as herein described.

2 Drawing Sheets

BACKGROUND AND SUMMARY OF INVENTION

Hops are grown commercially for use in flavoring beers, stouts and ales. Lupulin glands inside female hop cones provide the resins and essential oils which are the primary components of the hop flavor each variety imparts to beers, stouts, and ales. New hop varieties are evaluated for their growing characteristics, per acre hop cone yield (dried to approximately 8% moisture), the chemical composition of the resins and essential oils contained within the hop cone's lupulin glands, and the unique flavor each variety imparts to beers, stouts and ales. Only female hop plants produce cones containing lupulin glands, and thus only female hops have any commercial value. Male hop plants have no commercial value other than for use in breeding programs to create new varieties.

This invention relates to a new and distinct variety of hop and more particularly to as asexually reproduced hop variety selected from among hop plants resulting from a controlled cross pollination between an unpatented Galena female hop with unpatented John I. Haas, Inc. (Haas) male hop No. 833-53M.

Haas male hop No. 833-53M originated from a controlled cross pollination in 1982 between unpatented female hop USDA Accession No. 21055 and unpatented male hop USDA Accession No. 63015M.

The controlled cross pollination program resulting in the creation of the new hop variety, hereafter called "H87203-1", was performed in 1986 by Mr. Gene Probasco, a botanist employed by John I. Haas, Inc., in a Haas greenhouse located at 1112 North 16th Avenue, Yakima, Wash., 98902. Mr. Probasco discovered the H87203-1 variety in 1988, among the hop plants which were produced from the seeds resulting from the above described controlled cross pollination program.

The seeds from the cross between Galena female hop and Haas male hop No. 833-53M were planted in a Haas greenhouse in 1987. The most vigorous plants resulting from the cross were selected and planted in a Haas hop field located at Wada Farm, Yakima Golding Farms, Toppenish, Wash. This planting did not produce a crop during the planting year.

In 1988, as a result of chemical analysis and field observations of the hop plants resulting from the Galena female×Haas male 833-53M cross, Mr. Probasco was attracted to the H87203-1 hop plant for its unusually high percentage of beta acids, coupled with a relatively high percentage of alpha acids and a reasonable projected per acre cone yield. The per acre cone yield projections were based upon the cone production of the single H87203-1 hop plant observed in 1988. The H87203-1 plant was not asexually reproduced in 1988. The plant of this application has been repeatedly asexually reproduced by rooting cuttings at the address identified above. The clones of this plant have been observed to be identical to the original selection in every distinguishing characteristic and establish that the plant is genetically stable through successive generations by asexual propagation.

In 1988, brewing trials with hop cones from the new H87203-1 variety were conducted on a confidential and secret basis by a major brewery. For trade secret reasons, the identity of this brewery must remain confidential. The purpose of brewing trials is to ensure that beers, stouts, or ales produced using the new hop variety are indistinguishable in flavor, aroma and appearance from beers, stouts, or ales produced using the brewery's existing hop variety. This type of quality control is essential for a brewery to guarantee to its customers that a specific brand of beer, stout, or ale will consistently be the same when the new hop variety is used.

As a result of these 1988 brewing trials, the brewery decided to continue these tests of the new H87203-1 variety to determine the stability of its flavor, aroma and appearance characteristics over a period of years. Brewing trials with new varieties are usually conducted over a minimum of 3 years by major breweries before any decision is made as to whether or not the brewery will use the new variety in its brewing operation.

In 1989, the H87203-1 plant was not asexually reproduced. Further chemical analysis and field observations confirmed the new variety's unusually high percentage of beta acids, and its relatively high percentage of alpha acids and reasonable projected per acre cone yield. Brewing trials were again conducted by the same major brewery on a confidential basis, and resulted in the brewery deciding to continue trials with the new variety for a third year.

In 1990, second 2nd) generation rootstock from the H87203-1 variety was planted in a one acre test plot located at Wada Farm. This planting did not produce a crop during the planting year.

However, in 1990, chemical analysis and field observations of hop cones from the original H87203-1 variety again confirmed the new variety's unusually high percentage of beta acids, and its relatively high percentage of alpha acids and reasonable projected per acre cone yield. A third year of brewing trials by the same major brewery resulted in the brewery deciding to continue tests for a fourth year, with the fourth year tests to be conducted on hop cones from second generation plants.

In 1991, the first harvestable crop of the second (2nd) generation plants in the one-acre test plot provided additional information supporting the per acre cone yield projections made from the original H87203-1 plant identified in 1988 and confirmed the unusually high beta acids percentage characteristic of the new variety. The analytical data from chemical analysis of multiple random samples from bales of cones harvested from the one acre test plot showed an average beta acids percentage of 10.70% (ASBC spectrophotometric method). The first year per acre cone production for this one acre test plot was well within the average range of per acre cone production for a commercially viable hop variety. It is important to note that first year per acre cone yields in Washington state typically are lower than normal per acre yields for Washington state hop fields in subsequent years. Consequently, the per acre cone yield observations made from this first year one acre test plot were used to merely project anticipated normal yields for the new variety.

In 1991, the major brewery performed brewing trials of the first year crop of the second (2nd) generation plants in the one acre test plot. These tests were successful and the brewery decided to continue trials on beers brewed with hop cones from second (2nd) and third (3rd) generation plants in 1992.

Also,in 1991, John I. Haas, Inc., performed the first year trials of hexane extraction of the soft resins which include alpha acids and beta acids (hereafter "alpha acids extraction") on bales of the H87203-1 hop variety from the first crop produced from the one acre test plot. These initial extraction trials were successful because Haas was able to extract a minimum of 93% of the alpha acids present in the H87203-1 hop cones. John I. Haas, Inc. requires that a minimum of 93% of alpha acids be extractable from a new hop variety in order for the new variety to be considered potentially commercially viable.

In 1992, second (2nd) and third (3rd) generation rootstock from the H87203-1 variety was planted in a larger test plot of approximately 10 acres (large acreage test plot) at a John I. Haas, Inc. farm located at Toppenish, Wash. This planting did not yield a crop in 1992.

Also in 1992, the second (2nd) generation rootstock in the one acre test plot at Wada Farm was subjected to a second year of field observation and chemical analysis. In 1992, the second year per acre cone production from the one acre test plot was again well within the range of per acre cone production for a commercially viable hop variety.

The 1992 analytical data from chemical analysis of multiple random samples from bales of cones harvested from one acre test plot showed an average beta acids percentage of 11.10%. The second year hexane extraction trials confirmed again that Haas was able to consistently extract a minimum of 93% of the alpha acids present in second (2nd) generation H87203-1 hop cones. The 1992 brewing trials with this new variety have not yet been completed.

All of the testing and evaluation of the H87203-1 variety's growing characteristics, per acre hop cone yield, analytical data and soft resin (alpha acids) extraction tests were carried out on hop farms, laboratory facilities, and industrial extraction facilities which are wholly owned and controlled by John I. Haas, Inc. All of the brewing trials conducted by a major brewery on this new variety were conducted on a confidential and secret basis.

Based upon the field observations performed, and chemcial analytical data collected, during this testing and evaluation program from 1988 through 1992, it appears that second (2nd) and third (3rd) generation H87203-1 hop plants demonstrate genetic stability with respect to the new variety's novel characteristic of unusually high beta acids yields. Also, the new H87203-1 variety demonstrates genetic stability with respect to the production of commercially viable per acre hop cone yields.

This new hop variety has been carefully compared to its unpatented female parent Galena, and to its unpatented female grandparent USDA Accession No. 21055. (Please note that the hop industry does not make or rely upon any comparisons between new varieties and their male parents or male grandparents, because male hops have no commercial value). The primary difference between the new H87203-1 variety and its female parent and grandparent varieties is the unusually high beta acids percentages in bales of harvested hop cones.

THE DRAWINGS

The accompanying drawings illustrate the cones and leaves of the new H87203-1 hop variety:

The top photograph of Sheet 1 depicts mature cones, late season foliage and stems of the plant of this invention.

The bottom photograph of Sheet 1 depicts, at close range, the cone and leaf arrangement.

The top photograph of Sheet 2 depicts a lateral, and the arrangement of cones and leaves.

The bottom photograph of Sheet 2 illustrates a typical mature specimen of the plant growing on a typical hop trellis to show canopy density and plant form.

DESCRIPTION OF THE VARIETY

This description contains information about all botanical and analytical chemical characteristics upon which the hop industry relies in identifying and distinguishing specific hop varieties. The anlaytical data used to describe this new variety is subject to some variation between different samples of this new variety, due to the maturity of the hop cones sampled, climatic and growing conditions, geography, and other variables. For this reason the analytical values used to describe this new variety are expressed in terms of ranges or averages of values rather than absolute or fixed values.

GENERAL DESCRIPTIVE INFORMATION

I. Introduction

The hop plant, *Humulus lupulus,* is a perennial plant which produces annual climbing bines and a perennial crown. The bine, or vine as it is often called, can grow up to 25 feet in a single growing season. These bines climb in a clockwise direction without the aid of tendrils, but rather with the aid of hooked hairs known as tricomes. The bine of a mature hop may be one half to three quarters of an inch thick at the six foot height. In the spring the buds which have developed on the crown send out numerous shoots. Laterals grow from the axillary buds at each node along the main bine. The inflorescences develop from the axils of the laterals and each inflorescence becomes a single hop cone at maturity.

II. Roots

The hop crown will become woody with age, having heavy, rough bark after the first year. Much of the hop crown consists of branched stem tissue which lies buried at a shallow depth below the soils surface. This stem tissue, or rhizome, produces buds which in the spring develop into a mass of shoots. The crown also produces two types of roots; horizontal and vertical. The horizontal roots are fibrous, absorptive roots used for water uptake. The vertical roots, which develop from the horizontal roots, are thick and fleshy and serve as a carbohydrate storage organ.

III. Stems

The stems grow from the crown in early spring and twine around suitable support. Shoots of H87203-1 emerge from winter dormancy about the same time as the commercial variety Galena which is approximately the second week of April and then grow very rapidly similar to Galena. The stems are hexagonal in shape with the corners of the hexagon often protruding. On all sides of the stem are hairs, consisting mostly of silicates, and as these harden they become one or two sided hooks. Generally, the size of the stem at the six foot level is between ⅜" to ½" in dimeter. The main stem color is green and has purple stripes along the edges of the stem.

The hop bine can grow to a height of 20–24 feet. The trellis system on which the hop plant is grown is 18 feet high. Therefore, the bine will grow to a height of 18 feet and then will grow laterally along the trellis. The laterals which develop further up the bine are slightly longer, and can develop secondary branching. As cones develop the sidearms begin to recline (descend downward at a 106°–135° angle from central axis), therefore forming a head-shaped growth form near the trellis. This growth habit is described as "capitate," meaning that the majority of hop production is produced from lateral growth along the top wire of the trellising system. The remainder of the production is on the rest of the bine.

The first "training" for the variety H87203-1 is ideally the middle days of May. "Training" is a term used by growers to describe placement of vines on a support, one end of which is attached to the 18 foot high trellis, and the other end is secured into the soil. During training, the vines are placed on the support in a clockwise manner which is the natural helical growth pattern of all hop varieties.

IV. Leaves

Leaves of H87203-1 are borne in pairs at each node on the bine. On the stem of the plant the majority of the leaves are opposite in arrangement. Located at the petiole base are stipules which are interpetiolar in arrangement. The bine leaves are cordate in shape with 3 to 5 lobes, but mainly 3 lobes and palmate venation. The sinus cleft are deeply cut with leaf margins being smooth. The remainder of the leaf margins are serrate to dentate. The color is a green on the upper leaf surface and lighter green on the lower surface of the leaf. The leaves of H87203-1 are more of a yellow green color compared to the darker green leaves of her sister, H87207-2. Stiff fine hairs on the upper surface of the leaf give a dull appearance and rough texture. The lower surface bears many disc-shaped yellowish resin glands. The leaves are petiolate and said to be slightly channelled, therefore having a flat surface on the upper side of the petiole. The leaf petiole extends from the main vine in a reflexed position.

V. Laterals

The laterals, or sidearms as they are often called, originate from buds in the axils of leaves of stems. The sidearm position is "caulous," which means to grow more or less evenly spaced along the main bine.

VI. Cones

The inflorescences of H87203-1 begin to appear in late June and mature during the first week of September As they mature, they form a conelike structure, or strobile, referred to as a "cone." These inflorescences develop on a cranked axis and the cones form in pairs or clusters. The cones develop on the laterals from the top of the plant to approximately 40 inches above the ground. The cone consists of a central rachis or strig which bears numerous bracts and bracteoles. At the base of each bracteole is an ovary which, if pollinated, results in the lengthtening and thickening of the central strig. The plant variety H87203-1 is not fertilized, and therefore unseeded because the brewers do not want seeded cones.

The aroma of the cone is regarded by the inventor as pleasant. However, please note that hop aroma is not defined or measurable and therefore highly subjective.

The hop cone of H87203-1 is ovoid in shape and is tight when referring to its compactness. The tip of the cone is slightly pointed. The bract tip shape is cuspidate to attenuate, while the bracteole is acute to narrowly rounded. The central rachis or strig is considered to be thick as compared to the variety Cluster. The cone, and more specifically the bracetoles, contain numerous lupulin glands which contain resins which are the commercial value of the crop. The lupulin glands are cup shaped and white to creamy yellow in color. As the hop cone matures, the lupulin glands fill and form a globular shape and are golden yellow in color. The most important component of these resins is the alpha acid which gives beer its bitterness. Other components of the lupulin glands contribute to the flavor of the beer.

The cone numbers and cone size are direct factors in determining the yield of the variety. Climatic fluctuations, as well as cultural practices, soil type and fertility all have dramatic effects on yield. Cone uniformity with regard to size and level of maturity varies with the growing season. Cone shape is fairly uniform in the H87203-1 variety.

The hop cones of the H87203-1 variety are well adapted to mechanical harvest because of their compactness and ovoid shape. The cones do not shatter during harvest.

VII. Growth Characteristics

Growth of the annual stem is extremely rapid during a relatively short thirty day period during which the bine will grow approximately 20–24 feet in length. The extent of this rapid growth is very dependent on temperature, soil conditions and cultural practices.

VIII. Variability of Botanical Characteristics

Because of the variability of climate, temperature, soil conditions and cultural practices, the dimensions of the various components of a hop plant, including stems, cones, leaves, laterals and internodes vary tremendously from one year to the next, from one field to the next within the same year; and even from one plant to the next within the same field. This variation produces substantial overlapping of dimensions when comparing varieties and results in these dimensions having little use for comparing varieties.

IX. Propagation Methods

Asexual reproduction assures genetic stability and is used for increasing plant rootstock numbers to provide sufficient plants for commercial hop production. Sexual reproduction by this plant would result in genetic variability and therefore is undesirable other than for breeding purposes. The propagation methodology utilizes 1 to 2 inch vegetative cuttings, which are treated with a rooting hormone and planted in potting media in greenhouses. The treated cuttings are grown in greenhouses under rigorously controlled conditions, including without limitation control of temperature, humidity, light intensity, and day length conditions.

DETAILED DESCRIPTIVE INFORMATION

Following is a detailed description of the botanical and analytical chemical characteristics of the new variety. The information for the following botanical description was either collected or verified during the growing season of 1993 in the growing area west of Toppenish, Wash. These botanical characteristics, and to a lesser degree the analytical chemical characteristics, are dependent on cultural practices and climatic conditions and can vary with location and season:

1. Parentage: A hop plant originating from a controlled cross pollination between an unpatented Galena female hop with unpatented Haas male hop No. 833-53M.
2. Locality where grown and observed: Toppenish Wash.
3. Dates of first and last harvest: Approximately August 28 and September 10, respectively, in Toppenish, Wash.
4. Plant: Green vigorous, climbing vine.
   *Stripe.*—Purple.
   *Stipule direction.*—Down.
   *Plant shape.*—Capitate.
   *Leaf arrangement.*—Opposite.
   *Number of leaf lobes.*—3 or 5 lobes (mostly 3).
   *Leaf margin.*—Dentate.
   *Lateral.*—35 inches average.
   *Internode length.*—11.5 inches average.
5. Cone characteristics:
   *Bract tip shape.*—Cuspidate to attenuate.
   *Bract tip position.*—Loosely appressed.
   *Bracteole tip shape.*—Acute to narrowly rounded.
   *Compactness.*—Tight.
   *Shape.*—Ovoid.
   *Cone length.*—1.5 inches average.
   *Cone tip shape.*—Slightly pointed.
   *Strig.*—Thick.
   *Yield per acre.*—2200 to 2600 pounds/acre.
   *Maturity.*—Medium.
6. Color characteristics: Fall color characteristics are unknown because the leaves are totally removed and destroyed during the harvesting procedure. Using the Pantone Color Specifier 747XR from the Pantone Library of Color No. 1, the following color characteristics for H87203-1 have been determined.
   *Leaf upper surface.*—350U.
   *Leaf lower surface.*—363U.
   *Bine background.*—383U.
   *Bine stripe.*—1605U.
   *Cone bracteole.*—383U.
   *Cone bract.*—377U.
   *Sidearm stem.*—377U.
   *Sidearm stripe (if red).*—167U.
   *Sidearm stripe (if green).*—384U.
7. Analytical data of cones:
   *% Alpha acids (bale).*—13.5 to 15.5 (ASBC spectrophotometric method).
   *% Beta acids (bale).*13 9.5 to 11.5 (ASBC spectrophotometric method).
   *Alpha beta ratio.*—1.34 to 1.42.

*Analytical data determined on hops with approximately 8% cone moisture.

*Cohumulone (% of alpha acids).*—Average 35.0.
   *Colupulone (% of beta acids).*—Average 62.0.
   *Storage Characteristics*.—20.0% transformation after 6 months at 22 C. (Based on USDA Hop Storage Index).
   *Total oils (mls/100g)***.—Average 1.5.

**Analytical data determined on hops with approximately 8% cone moisture.

*Humulene (% of total oils).*—Average 13.0.
   *Caryophyllene (% of total oils).*—Average 11.0.
   *Humulene/caryophyllene ratio.*—Average 1.2.
   *Farnesene (% of total oils).*—0.0 (zero).
   *Myrcene (% of total oils).*—Average 40.0.
   *Lupulun (% of total cone weight).*—Average 32.
8. Analytical data of lupulin:
   *% Alpha acids.*—Average 42.0.
   *% Beta acids.*—Average 32.0
9. Disease resistance: The variety H87203-1 is moderately susceptible to downy mildew, it should be noted that there is no known resistance to the desease in any variety of hop. H87203-1 is tolerant to strains of verticillium wilt found in the state of Washington growing area. H87203-1 is also tolerant to the viruses found in the USA growing areas as well as to the major soil born pests including Phytophera root rot.
10. Regional adaptation: The H87203-1 variety is principally adapted to the drier growing region of the United States, specifically includin the Toppenish, Wash. area, and to other relatively dry growing regions with similar climatic and daylight/daylength conditions.
11. Plodiy: The genetic make up of H87203-1 is Galena X 833-53M (21055×63015M). Boeth parents are diploid, thus makinng H87203-1 a diploid plant. It is a full sister of the variety H87207-2. Because it is duploid this plant is capable of reproduction either by asexual or sexual reproduction.

12. Life expectancy: Life expectancy of this variety is not known, but presumed to be theoretically indefinite, similar to other varieties of the same species.
13. Use: Flavoring for beers, stouts, and ales.
14. Virus and propagation status:

H87203-1 rootstock has been virus-tested and is virus free. Propagatable plant material exists.

DISTINGUISHING CHARACTERISTICS

There are a few characteristics which are less variable and can be useful in comparing varieties. These include the direction of the stipules, color of the bind edges (stripes), the shapes and colors of the cones, and the analytical data of the cones. The following observations were taken in the Toppenish growing area during the 1993 season.

H87203-1 has several characteristics which distinguish it from its sister, H87207-2. The stipular direction on the plant H87203-1 is deflexed (bent abruptly downward) compared H87207-2, in which the stipular direction is inflexed (facing upward). Leaves of the variety H87203-1 are three to five lobes, but maintly three lobed. In contrast, H87207-2 have three to five lobed leaves but are mainly 5 lobed. H87203-1 and H87207-2 both have green bines with purple stripes. This characteristic being similar in both sisters would not help in identifying H87203-1 from H87207-2, but would help to distinguish the two sisters from other hop varieties which may not have the purple stripe.

Lateral lengths and internode lengths of H87203-1 are greater than for H87207-2.

Harvest dates of the variety H87203-1 are considered to be medium. The cones of this variety are similar to Galena in ease of picking. Drying times are slightly longer than the variety Galena, approximately equal to that of H87207-2, and shorter than H87311-3. Comparison of the two sisters regarding analyical data of the cones shows a difference in the percentages of certain components making up the total oils. H87203-1 has a higher amount of caryophylene than her sister while the amounts of humulene are similar. This makes the humulene/caryophylene ratio of H87203-1 about 1.2 compared to a ratio of 1.9 for her sister.

High percentages of beta acids distinguish H87203-1 and her sister from all other commercial varieties.

I claim:

1. A new variety of hop plant substantially as herein shown and described characterized particularly as to novel by its cones' usually high percentage of beta acids when compared to its female parent variety Galena (unpatented).

* * * * *

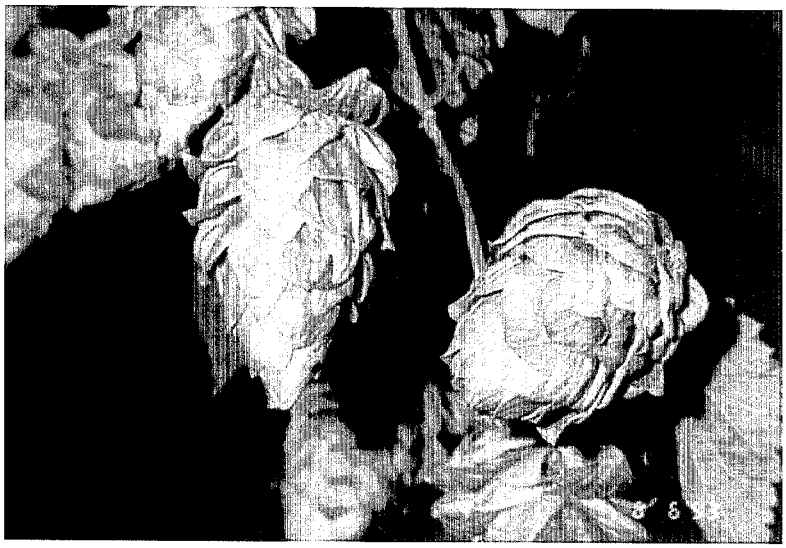
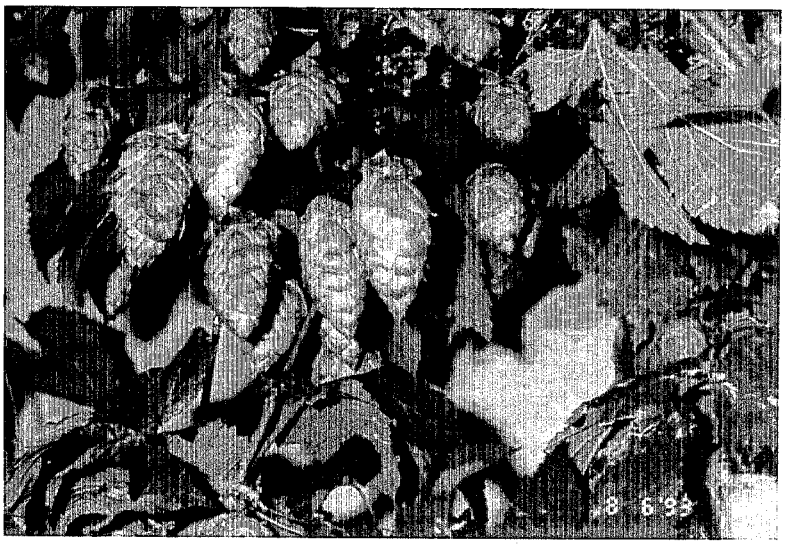

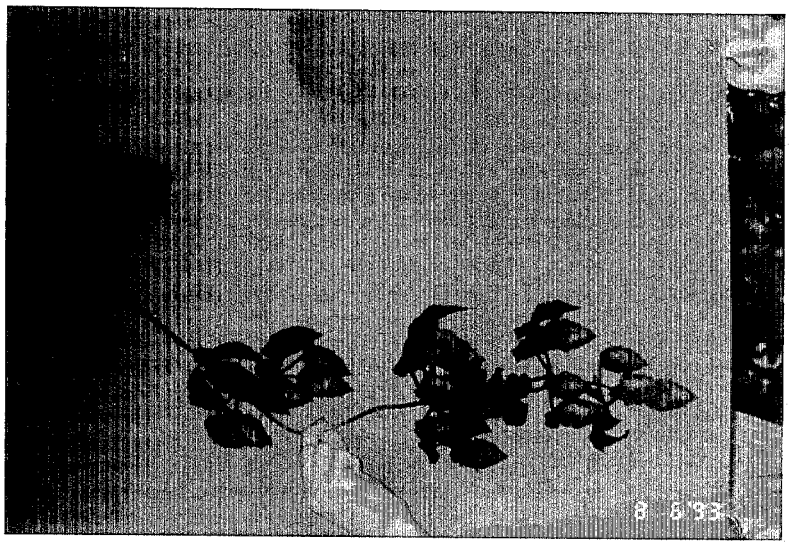
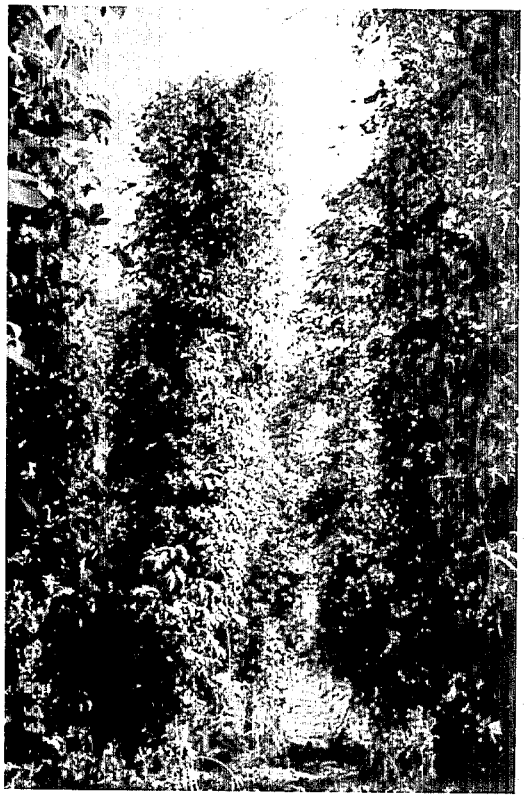

UNITED STATES PATENT AND TRADEMARK OFFICE

CERTIFICATE OF CORRECTION

PATENT NO. : Plant 8,824

DATED : July 5, 1994

INVENTOR(S) : Gene Probasco

It is certified that error appears in the above-indentified patent and that said Letters Patent is hereby corrected as shown below:

On the title page item [54], after the word "named", change "37" to --"--.

On the abstract, line 2, change "corss" to --cross--.

column 8, line 30, after the word "(bale)" insert --*--.

column 8, line 32, after the word "(bale)", change "13" to --*--.

column 8, line 34, after the word "ratio" insert --*--.

column 8, line 40, change "**" to --°--.

column 8, line 67, change "plodiy" to --ploidy--.

column 10, line 26, change "novel" to --novelty--.

Signed and Sealed this

Eighteenth Day of October, 1994

*Attest:*

Bruce Lehman

BRUCE LEHMAN

*Attesting Officer*

*Commissioner of Patents and Trademarks*